Patent Number: 5,068,236
Date of Patent: Nov. 26, 1991

[54] XANTHINE DERIVATIVES

[75] Inventors: Fumio Suzuki, Mishima; Junichi Shimada, Shizuoka; Kazuhiro Kubo; Tetsuji Ohno, both of Shizuoka, all of Japan; Akira Karasawa, Huntingdon Valley, Pa.; Akio Ishii; Hiromi Nonaka, both of Shizuoka, Japan

[73] Assignee: Kyowa Hakko Kogyo Co., Ltd., Tokyo, Japan

[21] Appl. No.: 486,831

[22] Filed: Mar. 1, 1990

[30] Foreign Application Priority Data

Mar. 6, 1989 [JP] Japan ................................ 1-53376
Sep. 1, 1989 [JP] Japan ................................ 1-226643

[51] Int. Cl.$^5$ .................... A61K 31/52; C07D 473/00
[52] U.S. Cl. .................................. 514/263; 544/267; 544/273; 544/272
[58] Field of Search ............... 514/263; 544/267, 272, 544/273

[56] References Cited

U.S. PATENT DOCUMENTS

| | | | |
|---|---|---|---|
| 3,624,215 | 11/1971 | Stein et al. | 424/253 |
| 3,624,216 | 11/1971 | Stein et al. | 424/253 |
| 4,299,832 | 11/1981 | Brown et al. | 424/253 |
| 4,546,182 | 10/1985 | Kjellin et al. | 544/273 |
| 4,558,051 | 12/1985 | Sunshine et al. | 514/261 |

FOREIGN PATENT DOCUMENTS

| | | |
|---|---|---|
| 724173 | 12/1965 | Canada . |
| 051458 | 8/1986 | European Pat. Off. . |
| 0256692 | 2/1988 | European Pat. Off. . |
| 2091249 | 7/1982 | United Kingdom . |

OTHER PUBLICATIONS

Chemical Abstract vol. 58 (1963) 10218b of von Schuh et al. German Patent 1,140,581.
The Merck Index, 10th ed., 9114 (1983).
J. Am. Chem. Soc., vol. 75, 114 (1953).
J. Med. Chem., vol. 14, No. 12, 1202 (1971).
Brit. J. Pharm., vol. 97, 502P (1989).
Brit. J. Pharm., vol. 96, 31P (1989).

*Primary Examiner*—Mukund J. Shah
*Assistant Examiner*—Matthew V. Grumbling
*Attorney, Agent, or Firm*—Fitzpatrick, Cella, Harper & Scinto

[57] ABSTRACT

Novel xanthine compounds represented by the following formula:

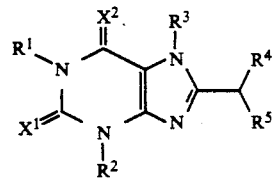

and pharmaceutically acceptable salts thereof have a diuretic action, a renal-protecting action and a vasodilative action.

The compounds are useful as a diuretic, a renal-protecting agent and an antihypertensive agent.

5 Claims, No Drawings

XANTHINE DERIVATIVES

BACKGROUND OF THE INVENTION

The present invention relates to a novel xanthine derivative having a diuretic action, a renal-protecting action and a vasodilative action.

Heretofore, theophylline, i.e., 1,3-dimethylxanthine has been known as a diuretic, a vasodilator, etc. [The Merck Index, 10th edition, 9114 (1983)].

Theophylline analogues represented by the following general formula (I) wherein both $R^4$ and $R^5$ are alkyl have a diuretic action, as disclosed in East German Patent No. 31,772 [Chem. Abst., 63, 18120d (1965)] (CA-724,173A); J. Am. Chem. Soc., 75, 114 (1953) and J. Med. Chem., 14, 1202 (1971), and also have a bronchodilative action, as disclosed in Japanese Published Unexamined Patent Application Nos. 166191/81 (U.S. Pat. No. 4,546,182), 163381/82 (GB-2091249A) and 41478/88 (EP-256692A). Furthermore xanthine derivatives having an anti-inflammatory action and other activities are disclosed in Japanese Published Unexamined Patent Application No. 66583/80 (U.S. Pat. No. 4,299,832); Japanese National Publication of translated version No. 500666/86 (U.S. Pat. No. 4,558,051); U.S. Pat. Nos. 3,624,215 and 3,624,216.

SUMMARY OF THE INVENTION

The present invention provides a novel xanthine derivative represented by the formula (I) wherein $R^4$ and $R^5$ are alicyclic alkyls or aryls and having a diuretic action, a renal-protecting action, a vasodilative action, etc.

The present invention relates to a xanthine derivative represented by the following general formula (I):

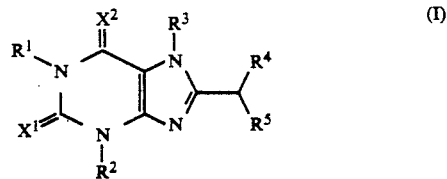

wherein each of $R^1$, $R^2$ and $R^3$ independently represents hydrogen or lower alkyl; each of $R^4$ and $R^5$ independently represents substituted or unsubstituted alicyclic alkyl, or substituted or unsubstituted aryl; and each of $X^1$ and $X^2$ independently represents oxygen or sulfur [hereinafter referred to as "Compound (I)" and compounds with other formula numbers are likewise referred to], or its pharmaceutically acceptable salt.

DETAILED DESCRIPTION OF THE INVENTION

In the definition of the respective groups in the formula (I), the lower alkyl includes straight or branched alkyl having 1 to 6 carbon atoms, for example, methyl, ethyl, n-propyl, isopropyl, n-butyl, isobutyl, sec-butyl, tert-butyl, n-pentyl, neopentyl, n-hexyl, etc. The alicyclic alkyl includes those having 3 to 8 carbon atoms, for example, cyclopropyl, cyclobutyl, cyclopentyl, cyclohexyl, cyclooctyl, etc. The aryl includes phenyl, naphthyl, etc. The substituent on the alicyclic alkyl and aryl independently includes lower alkyl, hydroxy, lower alkoxy, halogen, amino, nitro, etc., and the number of the substituents is 1 to 3. As the lower alkyl and the alkyl moiety in the lower alkoxy, mention may be made of the same groups as defined in the aforementioned lower alkyl. The halogen includes fluorine, chlorine, bromine and iodine.

The pharmaceutically acceptable salt of Compound (I) includes pharmaceutically acceptable acid addition salt, metal salt, ammonium salt, organic amine addition salt, amino acid addition salt, etc.

The pharmaceutically acceptable acid addition salt of Compound (I) includes inorganic acid salt such as hydrochloride, sulfate, phosphate, etc., and organic acid salt such as acetate, maleate, fumarate, oxalate, citrate, etc.

The pharmaceutically acceptable metal salt includes alkali metal salt such as sodium salt, potassium salt, etc., alkaline earth metal salt such as magnesium salt, calcium salt, etc., and also aluminum and zinc salts.

The ammonium salt includes salts of ammonium, tetramethylammonium, etc. The pharmaceutically acceptable organic amine addition salt includes addition salts of morpholine, piperidine, etc., and the pharmaceutically acceptable amino acid addition salt includes addition salts of lysine, glycine, phenylalanine, etc.

A process for producing the compounds of the present invention will be described below.

Compound (Ia) which is Compound (I) wherein $R^3$ is hydrogen, can be produced by the following production steps:

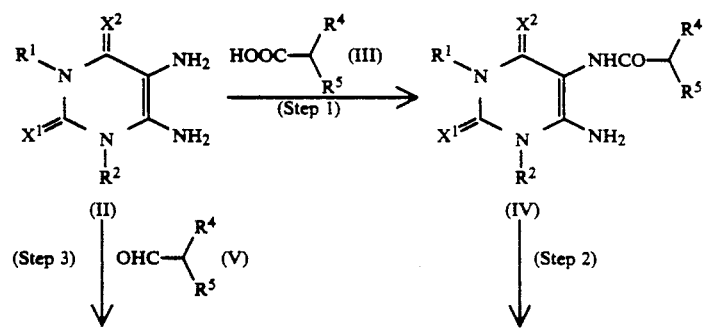

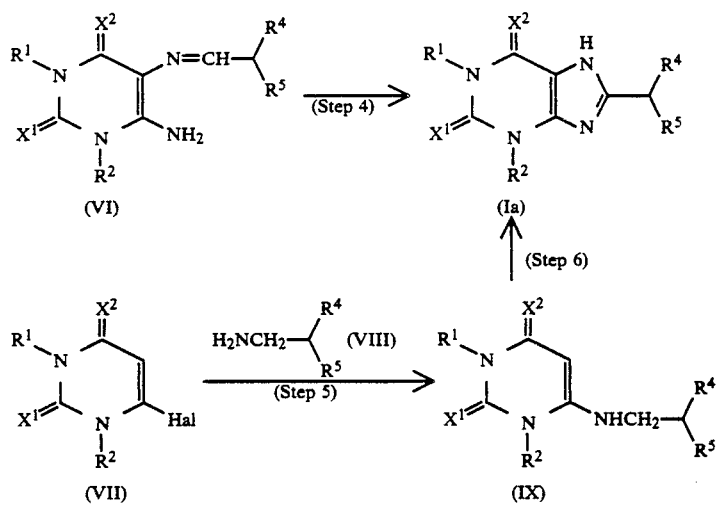

wherein Hal represents halogen such as chlorine, bromine or iodine and $R^1$, $R^2$, $R^4$, $R^5$, $X^1$ and $X^2$ have the same meanings as defined above.

STEP 1

A Compound (IV) can be obtained by reacting a uracil derivative (II) obtained according to a well known process [for example, the process disclosed in Japanese Published Unexamined Patent Application No. 42383/84] with carboxylic acid (III) or a carboxylic acid reactive derivative.

The carboxylic acid reactive derivative includes acid halides such as acid chlorides, acid bromides, etc., active esters such as p-nitrophenyl ester, N-oxysuccinimide ester, etc., acid anhydrides commercially available or those formed from carbodiimides such as 1-ethyl-3-(3-dimethylaminopropyl)carbodiimide, diisopropylcarbodiimide, dicyclohexylcarbodiimide, etc.; mixed acid anhydrides with monoethyl carbonate, monoisobutyl carbonate, etc. and so forth.

The reaction of Compound (II) with Compound (III) can be carried out without any solvent at a temperature of 50° to 200° C. In the case of using the carboxylic acid reactive derivative, the reaction can be carried out according to a process usually used in the peptide chemistry. For example, the reaction solvent is properly selected from halogenohydrocarbons such as methylene chloride, chloroform, dichloroethane, etc., ethers such as dioxane, tetrahydrofuran, etc., dimethylformamide and dimethylsulfoxide, and if necessary water is used. The reaction temperature is −80° to 50° C., and the reaction is completed for 0.5 to 24 hours. Sometimes, the reaction may be favorably carried out, if necessary, in the presence of an additive such as 1-hydroxybenzotriazole, etc., or a base such as pyridine, triethylamine, dimethylaminopyridine, N-methylmorpholine, etc. Furthermore, the carboxylic acid reactive derivative may be formed in the reaction system and used without isolation.

STEP 2

A desired Compound (Ia) with a closed ring can be obtained from Compound (IV) by the reaction in the presence of a base (process A), by treatment with a dehydrating agent (process B), or by heating (process C).

As the preferable base in the process A, alkali metal hydroxides such as sodium hydroxide, potassium hydroxide, etc. can be exemplified. As the reaction solvent, water, lower alcohols such as methanol, ethanol, etc., ethers such as dioxane, tetrahydrofuran, etc., dimethylformamide, dimethylsulfoxide, etc. can be used alone or in combination. The reaction is carried out at a temperature of from room temperature to 180° C. and is usually completed for 10 minutes to 6 hours.

As the dehydrating agent for use in the process B, thionyl halides such as thionyl chloride, etc., and phosphorus oxyhalides such as phosphorus oxychloride, etc. can be used, and the reaction is carried out at a temperature of from room temperature to 180° C. without any solvent or in a solvent inert to the reaction, for example, halogenohydrocarbons such as methylene chloride, chloroform, dichloroethane, etc., dimethylformamide, dimethylsulfoxide, etc. and is usually completed for 0.5 to 12 hours.

In the case of process C, the Compound (Ia) can be obtained by heating Compound (IV) at a temperature of 50° to 200° C. in a polar solvent such as dimethylsulfoxide, dimethylformamide, Dowthermo A (product of Muromachi Kagaku Kogyo Kaisha, Ltd.), etc.

STEP 3

A schiff base (VI) can be obtained by reacting Compound (II) with aldehyde (V) in a mixed solvent such as a mixture of acetic acid with a lower alcohol such as methanol, ethanol, etc. at a temperature of −20° to 100° C.

STEP 4

A desired Compound (Ia) can be obtained by subjecting Compound (VI) to an oxidative cyclization reaction.

As the appropriate oxidizing agent, oxygen, ferric chloride, cerium$^{IV}$ ammonium nitrate, diethyl azodicarboxylate, etc. can be exemplified. The reaction is carried out by heating Compound (VI) at from room temperature to 180° C. in the presence of the afore-mentioned oxidizing agent and, if necessary, in a solvent inert to the reaction, for example, a lower alcohol such as methanol, ethanol, etc., a halogenohydrocarbon such as methylene chloride, chloroform, etc., or an aromatic hydrocarbon such as toluene, xylene, nitrobenzene, etc.

STEP 5

A Compound (IX) can be obtained by reacting a uracil derivative (VII) obtained according to a well known process, for example, the process described in Japanese Published Unexamined Patent Application No. 5082/86 with an amine (VIII) in a solvent inert to the reaction, for example, a lower alcohol such as methanol, ethanol, etc., dimethylformamide, dimethylsulfoxide, etc. alone or in combination thereof at a temperature of 50° of 150° C.

STEP 6

A Compound (Ia) can be obtained by reacting a Compound (IX) with a nitrosating agent such as a nitrite derivative such as sodium nitrite, isoamyl nitrite, etc. under an acidic condition of dilute hydrochloric acid, etc. in a solvent inert to the reaction, for example, a lower alcohol such as methanol, ethanol, etc. usually at a temperature of from room temperature to the boiling point of the solvent.

STEP 7

A Compound (Ib) which is Compound (I) wherein $R^3$ is a lower alkyl group can be obtained through the following step:

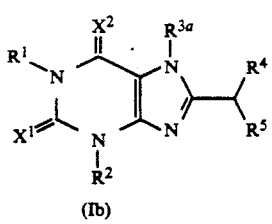

(Ia)

(Ib)

wherein $R^1$, $R^2$, $R^4$, $R^5$, $X^1$ and $X^2$ have the same meanings as defined above, $R^{3a}$ represents a lower alkyl in the definition of $R^3$ and L represents a leaving group.

As the leaving group, halogen such as bromine, iodine, etc., alkylsulfonyloxy such as methanesulfonyloxy, etc., and arylsulfonyloxy such as p-toluenesulfonyloxy, etc. can be exemplified.

A desired compound (Ib) can be obtained by reacting Compound (Ia) obtained in Steps 1 to 6 with an alkylating agent (X) preferably in the presence of a base. As the base, an alkali metal carbonate such as sodium carbonate, potassium carbonate, etc., an alkali metal hydride such as sodium hydride, etc., and an alkali metal alkoxide such as sodium methoxide, sodium ethoxide, etc. can be exemplified. The reaction is completed at a temperature of 0° to 180° C. usually for 0.5 to 24 hours.

STEP 8

Compound (Id) which is Compound (I) wherein $X^2$ is sulfur, can be obtained according the following step.

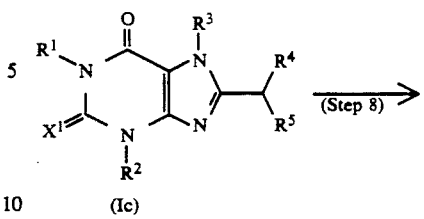

(Ic)

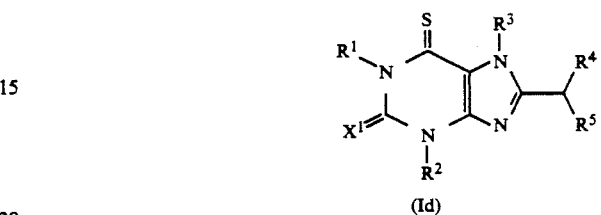

(Id)

wherein $R^1$, $R^2$, $R^3$, $R^4$, $R^5$ and $X^1$ have the same meanings as previously defined.

A desired Compound (Id) was prepared by reacting Compound (Ic) obtained by the above-mentioned steps which is Compound (I) wherein $X^2$ is oxygen, with an appropriate thionation reagent, in an inert solvent. As the thionation reagent, phosphorus pentasulfide and the like are mentioned. As the solvent, dimethylformamide, tetrahydrofuran, dioxane, etc. are mentioned, and preferably pyridine and the like are used. The reaction is carried out at a temperature of 50° to 180° C. for a period of 10 minutes to 12 hours.

The intermediates and the desired compound obtained according to the aforementioned processes can be isolated and purified by subjecting them to a purification process usually used in the organic synthetic chemistry, for example, filtration, extraction, washing, drying, concentration, recrystallization, various chromatographies, etc. The intermediates can be used in the successive reaction without any purification.

Salts of Compound (I) can be obtained by direct purification when Compound (I) can be obtained in a salt form, or by formation of a salt according to a usual procedure when the Compound (I) is obtained in a free form, and a subsequent purification.

Compound (I) and its pharmaceutically acceptable salts sometimes exist in an adduct form with water or various other solvents, and these adducts are included in the present invention.

Optical isomers may exist with respect to Compound (I), and all the possible stereoisomers and their mixtures are also included in the scope of the present invention.

Specific examples of Compound (I) are shown in Table 1, where compound numbers correspond to Example numbers appearing hereinafter:

TABLE 1

| Compound No. | R¹ | R² | R³ | R⁴/R⁵ | X¹ | X² |
|---|---|---|---|---|---|---|
| 1 | n-C₃H₇ | n-C₃H₇ | H | (cyclopropyl-CH) | O | O |
| 2 | n-C₃H₇ | n-C₃H₇ | H | (phenyl-CH-phenyl) | O | O |
| 3 | n-C₃H₇ | n-C₃H₇ | H | (cyclopentyl-CH-phenyl) | O | O |
| 4 | n-C₃H₇ | n-C₃H₇ | H | (cyclopropyl-CH-phenyl) | O | O |
| 5 | n-C₃H₇ | n-C₃H₇ | H | (cyclopropyl-CH-C₆H₄-OCH₃) | O | O |
| 6 | n-C₃H₇ | n-C₃H₇ | H | (cyclopropyl-CH-C₆H₄-F) | O | O |
| 7 | n-C₃H₇ | n-C₃H₇ | H | (dicyclohexyl-CH) | O | O |
| 8 | n-C₃H₇ | n-C₃H₇ | H | (CH-(CH₃)₂ with cyclopropyl) | O | O |

TABLE 1-continued

| Compound No. | R¹ | R² | R³ | R⁴/R⁵ | X¹ | X² |
|---|---|---|---|---|---|---|
| 9 | n-C₃H₇ | n-C₃H₇ | H | (cyclopropyl-CH) | S | O |
| 10 | H | n-C₃H₇ | H | (cyclopropyl-CH) | O | O |
| 11 | n-C₃H₇ | n-C₃H₇ | CH₃ | (cyclopropyl-CH) | O | O |
| 12 | H | n-C₃H₇ | H | (cyclopropyl-CH) | O | S |
| 13 | n-C₃H₇ | n-C₃H₇ | C₂H₅ | (cyclopropyl-CH) | O | O |
| 14 | n-C₃H₇ | n-C₃H₇ | n-C₃H₇ | (cyclopropyl-CH) | O | O |

Compound (I) of the present invention and its pharmaceutically acceptable salts have a diuretic action, a renal-protecting action and a vasodilative action and thus Compound (I) is useful as a diuretic, a renal-protecting agent and an antihypertensive agent.

The pharmacological action of Compound (I) will be explained, referring to Test Examples.

TEST EXAMPLE 1

Diuretic Action

Wistar rats (male: 150–300 g) were starved for 18 hours prior to the administration of the test compound. A test compound (25 mg/kg) and saline (25 ml/kg) were orally administered to test rats and only saline was administered to control rats. Three groups, each group consisting of 3 rats, were used for each test compound Urine was collected for 6 hours after the administration. Urine volume was measured and the electrolytes (Na and K) in the urine were determined with a flame photometer (775A, Hitachi, Ltd., Japan). The results are shown in Table 2.

All parameters are expressed as relative values of control. The compound Nos. 1, 4 and 11 exhibited more potent activity in the urine volume and have much higher ratios of Na to K than the reference compounds.

TABLE 2

| Compound No. | Urine amount (%) | Na+ excretion (%) | K+ excretion (%) | Na+/K+ |
|---|---|---|---|---|
| (Control) | 100 | 100 | 100 | 1.00 |
| 1 | 244 | 216 | 127 | 1.71 |
| 2 | 102 | 96 | 88 | 1.08 |
| 3 | 128 | 129 | 101 | 1.28 |
| 4 | 198 | 221 | 123 | 1.83 |
| 8 | 124 | 119 | 113 | 1.05 |
| 11 | 280 | 180 | 92 | 1.46 |
| Aminophylline*[1] (Reference compound) | 134 | 189 | 117 | 1.62 |
| Furosemide*[2] (Reference compound) | 175 | 164 | 157 | 1.05 |

*[1]The Merck Index, 10th edition, page 476 (1983)
*[2]The Merck Index, 10th edition, page 4189 (1983)

TEST EXAMPLE 2

Renal-Protecting Action (Glycerol-Induced Renal Failure Model)

A renal failure is a state where the renal function is lowered and the stationary state of a body fluid can be no more maintained. It is known that an acute renal failure characteristic of uriniferous tubule disorder is caused by subcutaneous or intramuscular injection of glycerol to rats [Can. J. Physiol. Pharmacol., 65, 42 (1987)].

Wistar rats (male) were kept deprived of water for 18 hours, and served for the test. A test compound was intraperitoneally administered to the rats (dosage: 10 mg/kg) and the rats were anesthetized with ether and 50% glycerol was subcutaneously administered (dosage: 0.8 ml/100 g) to the rats, pinching the dorsal skin. Twenty four hours after the administration of glycerol, the rats were anesthetized with ether and 5 ml of blood was collected from the abdominal aorta. The collected blood was allowed to stand for 30 minutes or longer and then centrifuged at 3,000 rpm for 10 minutes, and the serum creatinine was measured by creatinine test Wako (Jaffe method).

On the other hand, the left kidneys of the blood-sampled rats were removed and placed in formalin-filled vial bottles, and used as samples for the pathological examination.

According to the test results, Compound Nos. 1, 8 and 11 significantly suppressed an increase in the serum creatinine at a dosage of 10 mg/kg [i.p.] (Compound No. 1: $p<0.05$; Compound No. 8: $p<0.001$; compound No. 11: $p<0.001$), whereas aminophylline had no substantial effect of suppressing the increase. On the contrary, furosemide showed a tendency to increase the serum creatinine. The pathological examination of removed kidneys indicates that compounds Nos. 1, 8 and 11 also significantly improved the state of kidneys.

Compound (I) or its pharmaceutically acceptable salts can be used as such or in various medicament forms. The present pharmaceutical composition can be prepared by uniformly mixing an effective amount of Compound (I) or its pharmaceutically acceptable salts as an active component with a pharmaceutically acceptable carrier. The pharmaceutical composition is desirably in a unit dosage form applicable to oral or injection administration.

In the preparation of pharmaceutical compositions in an oral dosage form, some useful, pharmaceutically acceptable carrier can be used. For example, liquid, orally administerable compositions such as suspension compositions or syrup compositions can be prepared with water, a saccharide such as sucrose, sorbitol, fructose, etc., a glycol such as polyethyleneglycol, propyleneglycol, etc., an oil such as sesame oil, olive oil, soybean oil, etc., an antiseptic such as p-hydroxybenzoic acid esters, etc., and a flavor such as strawberry flavor, peppermint, etc. Powder, pills, capsules and tablets can be prepared with a vehicle such as lactose, glucose, sucrose, mannitol, etc., a disintegrator such as starch, sodium alginate, etc., a lubricant such as magnesium stearate, talc, etc., a binder such as polyvinyl alcohol, hydroxypropyl cellulose, gelatin, etc., a surfactant such as fatty acid esters, etc., a plasticizer such as glycerin, etc. and so forth. Tablets and capsules are most useful unit for oral administration because of easy administration. In the preparation of tablets or capsules, a solid pharmaceutical carrier is used.

Injection solutions can be prepared with a carrier such as distilled water, saline solution, glucose solution, or a mixture of saline solution and glucose solution.

Effective dosage and number of administration of Compound (I) or its pharmaceutically acceptable salts depend on the administration route and ages, body weights, symptoms, etc. of patients, and it is preferable to usually administer Compound (I) at a dosage of 1 to 50 mg/kg per day in 3 to 4 divisions.

The present invention will be described below, referring to Examples.

EXAMPLE 1

8-(1,1-Dicyclopropylmethyl)-1,3-dipropylxanthine (Compound No. 1)

At first, 1.40 g (10 mmol) of 1,1-dicyclopropylacetic acid was dissolved in 25 ml of pyridine, and 0.78 ml (11 mmols) of thionyl chloride was added thereto. Then, the mixture was stirred at 60° C. for 10 minutes. Then, a solution of 2.26 g (10 mmols) of 5,6-diamino-1,3-dipropyluracil in 15 ml of pyridine was added thereto under ice cooling, and the mixture was stirred for one hour. Then, the solvent was concentrated to approximately one-half under reduced pressure and the residue was poured into ice water and subjected to extraction with chloroform three times. The extract was washed with brine, and dried over anhydrous sodium sulfate and then the solvent was evaporated under reduced pressure. The residue was purified by silica gel column chromatography (eluent: 10% methanol/chloroform) to afford 2.33 g (yield: 67%) of amorphous 6-amino-5-(1,1-dichloropropyl)acetylamino-1,3-dipropyluracil [Compound (IV): $R^1=R^2=n\text{-}C_3H_7$; $R^4=R^5=$

$X^1=X^2=0$]

NMR (CDCl$_3$; 90 MHz) δ (ppm) 7.71 (brs 1H), 5.52 (brs, 2H), 4.00–3.75 (m, 4H), 1.90–1.50 (m, 4H), 1.40–0.20 (m, 17H)

Then, 10 ml of phosphorus oxychloride was added to the thus obtained compound and the mixture was refluxed for two hours. After concentration under reduced pressure, the residue was poured into ice water and the pH was adjusted to 6.5 with an aqueous 2N sodium hydroxide solution. Then, the mixture was extracted with chloroform three times, and the combined extract was washed with brine and dried over anhydrous sodium sulfate, and then the solvent was evaporated under reduced pressure. The residue was purified by silica gel column chromatography (eluent: 30% ethyl acetate/hexane) and recrystallized from ethanol-water to afford 1.33 g (yield: 60%) of the captioned Compound No. 1 as a white needle crystal.

Melting point: 129.1–130.4° C.
Elemental analysis (C$_{18}$H$_{26}$N$_4$O$_2$)
Calculated (%): C 65.43, H 7.93, N 16.96,
Found (%): C 65.53, H 8.11, N 16.82.
IR (KBr) νmax (cm$^{-1}$): 1700, 1654, 1498
NMR (CDCl$_3$; 270 MHz) δ (ppm): 12.70 (brs, 1H), 4.13 (t, 2H), 3.97 (t, 2H), 1.90–1.60 (m, 5H), 1.50–1.35 (m, 2H), 1.10–0.90 (m, 6H), 0.75–0.60 (m, 2H), 0.50–0.20 (m, 6H)

EXAMPLE 2

8-(1,1-Diphenylmethyl)-1,3-dipropylxanthine

Compound No. 2

At first, 2.00 g (8.85 mmol) of 5,6-diamino-1,3-dipropyluracil was dissolved in 10 ml of pyridine and 2.45 g (10.6 mmol) of diphenylacetyl chloride was added thereto under ice cooling. After stirring for 40 minutes, the mixture was poured into ice water and extracted with toluene three times. The extract was successively washed with water, an aqueous saturated sodium bicarbonate solution and brine, and dried over anhydrous sodium sulfate. The solvent was evaporated under reduced pressure to afford 3.92 g of amorphous 6-amino-5-(1,1-diphenyl)acetylamino-1,3-dipropyluracil [Compound (IV): R$^1$=R$^2$=n-C$_3$H$_7$; R$^4$=R$^5$=

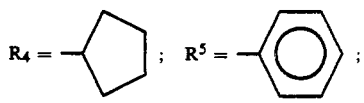

X$^1$=X$^2$=O]

Then, 36 ml of dioxane and 36 ml of an aqueous 2N sodium hydroxide solution were added to 3.62 g of the thus obtained compound and the mixture was refluxed under heating for 35 minutes. After cooling, the mixture was neutralized and extracted with chloroform three times. Then, the extract was washed with brine and dried over anhydrous sodium sulfate, and then the solvent was evaporated under reduced pressure. The residue was purified by silica gel column chromatography, and recrystallized from cyclohexane to afford 2.53 g (total yield: 86%) of the captioned Compound No. 2 as a white powder.

Melting point: 167.1–168.5° C.
Elemental analysis (C$_{24}$H$_{26}$N$_4$O$_2$)
Calculated (%): C 71.62, H 6.51, N 13.92,
Found (%): C 71.65, H 6.51, N 13.70.
IR (KBr) νmax (cm$^{-1}$): 1708, 1649, 1557, 1493
NMR (CDCl$_3$; 90 MHz) δ (ppm): 7.35–7.05 (m, 10H), 5.68 (s, 1H), 4.20–3.75 (m, 4H), 1.95–1.45 (m, 4H), 1.10–0.80 (m, 6H)

EXAMPLE 3

8-(1-Cyclopentyl-1-phenylmethyl)-1,3-dipropylxanthine

Compound No. 3

At first, 2.17 g (10.62 mmol) of 2-phenylcyclopentane acetic acid and 2.04 g (10.62 mmol) of 1-ethyl-3-(3-dimethylaminopropyl)carbodiimide hydrochloride were added to a solution of 2.00 g (8.85 mmol) of 5,6-diamino-1,3-dipropyluracil in 40 ml of dioxane and 20 ml of water and the mixture was stirred at room temperature for 4 hours while adjusting the pH to 5.5. The pH of the mixture was adjusted to pH 7.5, and then the mixture was extracted with chloroform three times, and the extract was washed with brine and dried over anhydrous sodium sulfate. The solvent was evaporated under reduced pressure. The residue was purified by silica gel column chromatography (eluent: 2% methanol/chloroform) to afford 1.73 g (yield: 47%) of amorphous 6-amino-5-(1-cyclopentyl-1-phenyl)acetylamino-1,3-dipropyluracyl [Compound (IV): R$^1$=R$^2$=n-C$_3$H$_7$;

X$^1$=X$^2$=O]

MS (m/e): 412, 253, 226, 225, 159, 91
NMR (CDCl$_3$; 90 MHz) δ (ppm): 7.50–7.00 (m, 5H), 5.22 (brs, 2H), 4.00–3.60 (m, 4H), 3.28 (d, 1H, J=11 Hz), 2.8–2.45 (m, 1H), 2.10–0.80 (m, 18H)

Then, 13 ml of phosphorus oxychloride was added to 1.28 g (3.11 mmol) of the thus obtained compound and the mixture was refluxed under heating for 30 minutes. Then, the mixture was concentrated under reduced pressure and the residue was poured into ice water. The pH was adjusted to 6.5 with an aqueous 2N sodium hydroxide solution. The mixture was extracted with chloroform three times and the extract was washed with brine and dried over anhydrous sodium sulfate. Then, the solvent was evaporated under reduced pressure, and the residue was purified by silica gel column chromatography (eluent: 25% ethyl acetate/hexane), and recrystallized from isopropanol-water to afford 730 mg (yield: 59%) of the captioned Compound No. 3 as a white powder.

Melting point: 136.6–138.1° C.
Elemental analysis (C$_{23}$H$_{30}$N$_4$O$_2$)
Calculated (%): C 70.02, H 7.66, N 14.20,
Found (%): C 69.91, H 7.77, N 14.14.
IR (KBr) νmax (cm$^{-1}$): 1703, 1654, 1496
NMR (CDCl$_3$; 270 MHz) δ (ppm): 12.80 (brs, 1H), 7.60–7.15 (m, 5H), 4.20–4.05 (m, 4H), 3.90 (d, 1H, J=11.0 Hz), 3.10–2.90 (m, 1H), 2.00–1.50 (m, 10H), 1.30–0.90 (m, 8H)

EXAMPLE 4

8-(1-Cyclopropyl-1-phenylmethyl)-1,3-dipropylxanthine

Compound No. 4

At first, 1.84 g (9.56 mmol) of 1-ethyl-3-(3-dimethylamino-propyl)carbodiimide hydrochloride was added at room temperature to a solution of 1.55 g (8.76 mmol) of 1-cyclopropyl-1-phenylacetic acid [Pestic. Sci., 11, 513 (1988)] and 1.80 g (7.96 mmol) of 5,6-diamino-1,3-dipropyluracil in 36 ml of dioxane and 18 ml of water and the mixture was stirred for 2 hours, while adjusting the pH to 5.5. The pH of the mixture is adjusted to 7.5, and the mixture was extracted with chloroform three times, and the extract was washed with brine and dried over anhydrous sodium sulfate. Then, the solvent was evaporated under reduced pressure and the residue was purified by silica gel column chromatography (eluent: 1.5% methanol/chloroform) to afford 2.07 g (yield: 61%) of amorphous 6-amino-5-(1-cyclopropyl-1-phenyl)acetylamino-1,3-dipropyluracil [Compound (IV): $R^1=R^2=n-C_3H_7$; $R^4=$

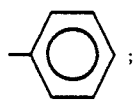

$R^5=$

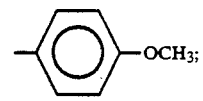

$X^1=X^2=O$]

NMR (CDCl$_3$; 90 MHz) δ (ppm): 7.70 (brs. 1H), 7.40–7.15 (m, 5H), 5.42 (brs, 2H), 4.00–3.65 (m, 4H), 2.93 (d, 1H, J=10 Hz), 1.95–1.25 (m, 5H), 1.10–0.20 (m, 10H)

Then, 30 ml of dioxane and 40 ml of an aqueous 1N sodium hydroxide solution were added to 1.90 g (4.95 mmol) of the thus obtained compound and the mixture was refluxed under heating for 15 minutes. After neutralization, the mixture was concentrated until the volume of the mixture was approximately two-thirds, and the residue was extracted with chloroform three times. The extract was washed with brine and dried over anhydrous sodium sulfate. Then, the solvent was evaporated under reduced pressure, and the residue was purified by silica gel column chromatography (eluent: 30% ethyl acetate/hexane) and recrystallized from cyclohexane to afford 1.77 g (yield: 93%) of the captioned Compound No. 4 as a white powder.

Melting point: 153.9–155.1° C.

Elemental analysis (C$_{21}$H$_{26}$N$_4$O$_2$)

Calculated (%): C 68.83, H 7.15, N 15.29,

Found (%): C 69.06, H 7.42, N 15.34.

IR (KBr) νmax (cm$^{-1}$): 1709, 1652, 1497

NMR (CDCl$_3$; 270 MHz) δ (ppm): 13.11 (brs. 1H), 7.50–7.40 (m, 2H), 7.35–7.15 (m, 3H), 4.12 (t, 2H), 3.98 (t, 2H), 3.46 (d, 1H, J=10.3 Hz), 1.95–1.65 (m, 5H), 1.05–0.90 (m, 6H), 0.80–0.65 (m, 2H), 0.50–0.35 (m, 2H)

EXAMPLE 5

8-[1-Cyclopropyl-1-(4-methoxyphenyl)methyl]-1,3-dipropylxanthine

Compound No. 5

The substantially same operations as in Example 4 were repeated using 1.57 g (7.61 mmol) of 1-cyclopropyl-1-(4-methoxyphenyl)acetic acid [Pestic. Sci., 11, 513 (1980)] and 1.56 g (6.92 mmol) of 5,6-diamino-1,3-dipropyluracil, to afford 1.72 g (yield: 53%) of amorphous 6-amino-5-[1-cyclopropyl-1-(4-methoxyphenyl)-]acetylamino-1,3-dipropyluracil [Compound (IV): $R^1=R^2=n-C_3H_7$; $R^4=$

$R^5=$

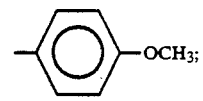—OCH$_3$;

$X^1=X^2=O$]

NMR (CDCl$_3$; 90 MHz) δ (ppm): 7.67 (brs. 1H), 7.28 (d, 2H, J=9 Hz), 6.83 (d, 2H, J=9 Hz), 5.43 (brs. 2H), 4.00–3.70 (m, 4H), 3.79 (s, 3H), 2.92 (d, 1H, J=10 Hz), 1.95–1.25 (m, 5H), 1.10–0.20 (m, 10H)

The substantially same operations as in Example 4 were repeated using 1.60 g (3.86 mmol) of the thus obtained compound, and recrystallization from isopropanol-water afforded 1.23 g (yield: 76%) of the captioned Compound No. 5 as a white needle crystal.

Melting point: 142.5–143.7° C.

Elemental analysis (C$_{22}$H$_{28}$N$_4$O$_3$)

Calculated (%): C 66.64, H 7.12, N 14.13,

Found (%): C 66.70, H 7.35, N 14.24.

IR (KBr) νmax (cm$^{-1}$): 1710, 1651, 1514, 1498

NMR (CDCl$_3$; 270 MHz) δ (ppm): 12.46 (brs, 1H), 7.38 (d, 2H, J=9.6 Hz), 6.85 (d, 2H, J=9.6 Hz), 4.11 (t, 2H), 3.98 (t, 2H), 3.78 (s, 3H), 3.42 (d, 1H, J=10.0 Hz), 1.90–1.60 (m, 5H), 1.10–0.95 (m, 6H), 0.80–0.60 (m, 2H), 0.50–0.30 (m, 2H)

EXAMPLE 6

8-[1-Cyclopropyl-1-(4-fluorophenyl)methyl]-1,3-dipropylxanthine

Compound No. 6

The substantially same operations as in Example 4 were repeated using 1.89 g (9.73 mmol) of 1-cyclopropyl-1-(4-fluorophenyl)acetic acid [Pestic. Sci., 11, 513 (1980)] and 2.00 g (8.85 mmol) of 5,6-diamino-1,3-dipropyluracil, to afford 1.91 g (yield: 49%) of amorphous 6-amino-5-[1-cyclopropyl-1-(4-fluorophenyl)-]acetylamino-1,3-dipropyluracil [Compound (IV); $R^1=R^2=n-C_3H_7$; $R^4=$

$R^5=$

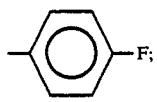

$X^1=X^2O$].

NMR (CDCl$_3$; 90 MHz) δ (ppm): 7.73 (brs, 1H), 7.33 (dd, 2H, J=5, 9 Hz), 7.01 (dd, 2H, J=9, 9 Hz), 5.42 (brs, 2H), 4.00–3.70 (m, 4H), 2.91 (d, 1H, J=10 Hz), 2.00–1.25 (m, 5H), 1.10–0.20 (m, 10H)

The substantially same operations as in Example 4 were repeated using 1.75 g (4.35 mmol) of the thus obtained compound, and recrystallization from isopropanol-water was carried out to afford 1.41 g (yield: 80%) of the captioned Compound No. 6 as a white needle crystal.

Melting point: 156.2–157.8° C.
Elemental analysis (C$_{21}$H$_{25}$FN$_4$O$_2$)
Calculated (%): C 65.61, H 6.55, N 14.57,
Found (%): C 65.57, H 6.70, N 14.69,
IR (KBr) νmax (cm$^{-1}$): 1710 1653 1510 1498
NMR (CDCl$_3$; 270 MHz) δ (ppm): 12.62 (brs, 1H), 7.45 (dd, 2H, J=5.3, 8.5 Hz), 7.01 (dd, 2H, J=8.5 8.5 Hz), 4.12 (t, 2H), 3.98 (t, 2H), 1.90–1.65 (m, 5H), 1.10–0.95 (m, 6H), 0.80–0.60 (m, 4H), 0.50–0.35 (m, 2H)

EXAMPLE 7

8-(1,1-Dicyclohexylmethyl)-1,3-dipropylxanthine

Compound No. 7

At first, 2.19 g (9.74 mmol) of 1,1-dicyclohexylacetic acid was dissolved in 30 ml of pyridine, and then 0.78 ml (11 mmol) of thionyl chloride was added thereto. The mixture was stirred at room temperature for 30 minutes, and then a solution of 2.00 g (8.85 mmol) of 5,6-diamino-1,3-dipropyluracil in 10 ml of pyridine was added thereto under ice cooling. The mixture was stirred for one hour. After addition of 50 ml of toluene thereto, the mixture was concentrated until the volume is reduced approximately to one-third and the residue was poured into ice water and extracted with chloroform three times. The extract was washed with brine and dried over anhydrous sodium sulfate. The solvent was evaporated under reduced pressure, and the residue was purified by silica gel column chromatography (eluent: 1% methanol/chloroform) to afford 3.79 g (yield: 99%) of amorphous 6-amino-5-(1,1-dicyclohexyl)acetylamino-1,3-dipropyluracil [Compound (IV); R$^1$=R$^2$=n-C$_3$H$_7$, R$^4$=R$^5$=

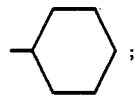

$X^1=X^2=0$].

NMR (CDCl$_3$; 90 MHz) δ (ppm): 7.19 (brs, 1H), 5.52 (brs, 2H), 4.00–3.70 (m, 4H), 2.10–0.75 (m, 33H)

Then, 35 ml of phosphorus oxychloride was added to 3.50 g (8.10 mmol) of the thus obtained compound and the mixture was refluxed under heating for 2 hours. After concentration under reduced pressure, the residue was poured into ice water and the pH was adjusted to 6.5 with an aqueous 2N sodium hydroxide solution. Then, the mixture was extracted with chloroform three times and the extract was washed with brine and dried over anhydrous sodium sulfate. The solvent was evaporated under reduced pressure and the residue was purified by silica gel column chromatography (eluent: 15% ethyl acetate/hexane), and recrystallized from cyclohexane to afford 2.58 g (yield: 77%) of the captioned Compound No. 7 as a white powder state.

Melting point: 198.3–200.1° C.
MS (m/e): 414 (M+), 332, 331, 289
IR (KBr) νmax (cm$^{-1}$): 1700, 1650, 1498
NMR (DMSO-d$_6$; 270 MHz) δ (ppm): 12.96 (brs, 1H), 3.97 (t, 2H), 3.83 (t, 2H), 2.45 (t, 1H, J=7.8 Hz), 1.90–0.60 (m, 32H)

EXAMPLE 8

8-[1,1-Di(2-methylcyclopropyl)methyl]-1,3-dipropylxanthine (diastereoisomer mixture)

Compound No. 8

The substantially same operations as in Example 7 were repeated using 980 mg (5.83 mmol) of 1,1-di(2-methylcyclopropyl)acetic acid and 1.20 g (5.30 mmol) of 5,6-diamino-1,3-dipropyluracil, to obtain 1.20 g (yield: 60%) of amorphous 6-amino-5-[1,1-di(2-methylcyclopropyl)]acetylamino-1,3-dipropyluracil [Compound (IV); R$^1$=R$^2$=n-C$_3$H$_7$; R$^4$=R$^5$=

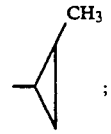

$X^1=X^2=0$]

NMR (CDCl$_3$; 90 MHz) ≠ (ppm): 7.58 (brs, 1H), 5.52 (brs, 2H), 4.00–3.75 (m, 4H), 2.00–0.20 (m, 25H)

885 mg (yield: 78%) of the captioned Compound No. 8 was obtained as a light yellow powder from 1.20 g (3.18 mmol) of the thus obtained compound in the substantially same manner as in Example 7.

Melting point: 67.2–70.3° C.
MS (m/e): 358 (M+), 303, 287
IR (KBr) νmax (cm$^{-1}$): 1700, 1655 (shoulder), 1650, 1498
NMR (CDCl$_3$; 270 MHz) δ (ppm): 12.65–12.30 (brm, 1H), 4.11 (t, 2H), 3.99 (t, 2H), 2.20–0.20 (m, 25H)
HPLC [AM-312(YMC 150 x 5φ), 50% acetonitrile-water, UV 271 nm, 2.0 ml/min]: Retention time (relative area); 16.9 min.(19), 17.8 min.(30), 19.7 min.(21), 20.5 min.(30)

EXAMPLE 9

8-(1,1-Dicyclopropylmethyl)-1,3-dipropyl-2-thioxanthine

Compound No. 9

The substantially same procedure as in Example 1 was repeated using 1.27 g (9.09 mmol) of 1,1-dicyclopropylacetic acid and 2.00 g (8.26 mmol) of 5,6-diamino-1,3-dipropyl-2-thiouracil [J. Med. Chem., 32, 1873 (1989)] to obtain 2.42 g (yield: 81%) of amorphous 6-amino-5-(1,1-dicyclopropyl) acetylamino-1,3-dipropyl-2-thiouracil [Compound (IV); R$^1$=R$^2$=n-C$_3$H$_7$; R$^4$=R$^5$=

$X^1 = S; X^2 = O$]

NMR (CDCl$_3$; 90 MHz) δ (ppm): 7.75 (brs, 1H), 5.70 (brs, 2H), 4.60–4.20 (m, 4H), 2.05–0.20 (m, 21H)

Then, the substantially same procedure as in Example 1 was repeated using 2.00 g (5.49 mmol) of the thus obtained compound, and recrystallization was carried out from ethanol-water to afford 1.09 g (yield: 57%) of the captioned Compound No. 9 as a white needle crystal.

Melting point: 153.8–156.4° C.
Elemental analysis (C$_{18}$H$_{26}$N$_4$OS)
Calculated (%): C 62.40, H 7.56, N 16.17,
Found (%): C 62.71, H 7.94, N 16.24.
IR (KBr) νmax (cm$^{-1}$): 1674, 1493, 1408
NMR (CDCl$_3$; 270 MHz) δ (ppm): 12.79 (brs, 1H), 4.69 (t, 2H), 4.57 (t, 2H), 2.00–1.70 (m, 5H), 1.50–1.35 (m, 2H), 1.10–0.95 (m, 6H), 0.80–0.60 (m, 2H), 0.50–0.20 (m, 6H)

EXAMPLE 10

8-(1,1-Dicyclopropylmethyl)-3-propylxanthine

Compound No. 10

The substantially same procedure as in Example 1 was repeated using 1.68 g (12.0 mmol) of 1,1-dicyclopropylacetic acid and 2.00 g (10.9 mmol) of 5,6-diamino-3-propyluracil to afford 1.07 g (yield: 51%) of 6-amino-5-(1,1-dicyclopropyl) acetylamino-3-propyluracil [Compound (IV): R$^1$=H; R$^2$=n-C$_3$H$_7$; R$^4$=R$^5$=

$X^1 = X^2 = O$] as a pale yellow powder.

NMR (DMSO-d$_6$; 90 MHz) δ (ppm): 10.55 (brs, 1H), 8.16 (brs, 1H), 6.05 (brs, 2H), 3.73 (t, 2H), 1.80–0.10 (m, 16H)

To 2.00 g (6.54 mmol) of the thus obtained compound were added to 40 ml of an aqueous 2N sodium hydroxide and 20 ml of dioxane. The mixture was refluxed under heating for two hours, cooled and neutralized. The neutral mixture was extracted three times with a 9:1 mixture of chloroform and methanol, and washed with brine. The mixture was dried over anhydrous sodium sulfate, and the solvent was evaporated under reduced pressure. The residue was purified by silica gel column chromatography (eluent: 2% methanol/chloroform), and recrystallized from ethanol to afford 859 mg (yield: 45%) of the captioned Compound No. 10 as a white crystal.

Melting point: 271.8–277.8° C.
IR (KBr) νmax (cm$^{-1}$): 1694, 1660, 1499
NMR (DMSO-d$_6$; 90 MHz) δ (ppm): 13.03 (brs, 1H), 10.92 (brs, 1H), 3.85 (t, 2H), 1.90–0.05 m, 16H)
MS (m/e): 288 (M+)

EXAMPLE 11

8-(1,1-Dicyclopropylmethyl)-1,3-dipropyl-7-methylxanthine

Compound No. 11

To a solution of 2.00 g (6.05 mmol) of Compound No. 1 obtained in Example 1 in 60 ml of dimethylformamide were added 2.09 g (15.1 mmol) of potassium carbonate and 0.75 ml (12.1 mmol) of methyl iodide. The mixture was stirred at 50° C. for one hour and cooled. Insoluble matters were filtered off, and the residue was concentrated under reduced pressure and 200 ml of water was added thereto. The aqueous solution was extracted three times with chloroform and the extract was washed with brine and dried over anhydrous sodium sulfate. The solvent was evaporated under reduced pressure, and the residue was purified by silica gel column chromatography (eluent: 20% ethyl acetate/hexane), and recrystallized from heptane to obtain 1.71 g (yield: 82%) of the captioned compound No. 11 as a white powder.

Melting point: 69.5–70.3° C.
Elemental analysis (C$_{19}$H$_{28}$N$_4$O$_2$)
Calculated (%): C 66.25, H 8.19, N 16.27,
Found (%): C 66.00, H 8.55, N 16.49.
IR (KBr) νmax (cm$^{-1}$): 1696, 1660, 1541, 1457
NMR (CDCl$_3$; 270 MHz) δ (ppm): 4.08 (t, 2H), 3.96 (t, 2H), 3.90 (s, 3H), 1.90–1.60 (m, 5H), 1.40–1.28 (m, 2H), 1.05–0.90 (m, 6H), 0.70–0.60 (m, 2H), 0.50–0.40 (m, 2H), 0.30–0.15 (m, 4H)

EXAMPLE 12

8-(1,1-Dicyclopropylmethyl)-3-propyl-6-thioxanthine

Compound No. 12

4.00 g (13.9 mmol) of Compound No. 10 obtained in Example 10 was refluxed together with 5.03 g (22.6 mmol) of phosphorus pentasulfide in 80 ml of pyridine for 3 hours, and cooled. The reaction mixture was poured into 250 ml of ice water. The precipitates were separated by filtration. The filtrate was concentrated until the volume is reduced to one-fourth. The precipitate was separated by filtration, and suspended in 80 ml of an aqueous 2N sodium hydroxide and a insoluble matter was filtered off. The filtrate was neutralized, and the precipitated crystal was recrystallized from ethanol-water to afford 3.52 g (yield: 83%) of the captioned compound No. 12 as a pale yellow needle crystal.

Melting point: 219.4–219.8° C.
IR (KBr) νmax (cm$^{-1}$): 1661, 1606, 1570, 1505
NMR (DMSO-d$_6$; 90 MHz) δ (ppm): 12.9 (brs, 1H), 12.1 (brs, 1H), 3.90 (t, 2H), 1.90–0.01 (m, 16H)
MS (m/e): 304 (M+)

EXAMPLE 13

7-Ethyl-8-(1,1-dicyclopropylmethyl)-1,3-dipropylxanthine

Compound No. 13

The substantially same procedure as in Example 11 was repeated using 2.00 g (6.5 mmol) of 8-(1,1-dicyclopropylmethyl)-1,3-dipropylxanthine obtained in Example 1 and 0.97 ml of ethyl iodide (12.1 mmol) to afford 1.53 g (yield: 71%) of the captioned Compound No. 13 as a pale yellow solid.

Melting point: 80.4–82.7° C.
IR (KBr) νmax (cm$^{-1}$): 1700, 1659, 1539, 1417

NMR (CDCl₃; 90 MHz) δ (ppm): 4.22 (q, 2H, J=7 Hz), 4.15–3.80 (m, 4H), 1.40 (t, 3H, J=7 Hz), 2.00–0.20 (m, 21H).

MS (m/e): 358 (M+)

EXAMPLE 4

8-(1,1-Dicyclopropylmethyl)-1,3-dipropyl-7-propylxanthine

Compound No. 14

The substantially same procedure as in Example 11 was repeated using 2.00 g (6.05 mmol) of 8-(1,1-dicyclopropylmethyl)-1,3-dipropylxanthine obtained in Example 1 and 1.18 ml of propyl iodide (12.1 mmol), and recrystallization was carried out from ethanol-water to afford 1.85 g (yield: 82%) of the captioned Compound No. 14 as a white crystal.

Melting point: 93.2–99.6° C.

IR (KBr) νmax (cm⁻¹): 1702, 1660, 1541, 1416

NMR (CDCl₃; 90 MHz) δ (ppm): 4.25–3.75(m, 6H), 2.00–0.20 (m, 26H)

MS (m/e): 372 (M+)

What is claimed is:

1. A xanthine compound represented by the following formula:

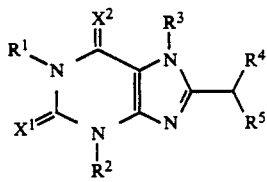

wherein each of $R^1$, $R^2$ and $R^3$ independently represents hydrogen or lower alkyl; each of $R^4$ and $R^5$ independently represents substituted or unsubstituted alicyclic alkyl, and each of $X^1$ and $X^2$ independently represents oxygen or sulfur, or its pharmaceutically acceptable salt.

2. The compound according to claim 1, wherein each of $R^4$ and $R^5$ is independently selected from the group consisting of cyclopropyl, 2-methylcyclopropyl, cyclopentyl, and cyclohexyl.

3. The compound according to claim 2, wherein both $R^1$ and $R^2$ are n-propyl and $R^3$ is hydrogen or methyl.

4. The compound according to claim 1, which is selected from the group consisting of 8-(1,1-dicyclopropylmethyl)-1,3-dipropylxanthine, 8-[1,1-di(2-methylcyclopropyl)methyl]-1,3-dipropylxanthine and 8-(1,1-dicyclopropylmethyl)-1,3-dipropyl-7-methylxanthine.

5. A diuretic, renal-protecting and vasodilative composition comprising a pharmaceutical carrier and, as an active ingredient, an amount of a xanthine compound as defined by claim 1, effective to have diuretic, renal protective and vasodilative activity, or a pharmaceutically acceptable salt thereof.

* * * * *